(12) United States Patent
Davis-Hoover et al.

(10) Patent No.: US 6,300,121 B1
(45) Date of Patent: Oct. 9, 2001

(54) METHOD FOR REDUCING BIOAVAILABILITY OF LEAD BY A LEAD-SEQUESTERING SOIL BACTERIUM

(75) Inventors: Wendy J. Davis-Hoover, West Chester; Stephen J. Vesper, Kettering, both of OH (US)

(73) Assignee: The United States of America as represented by the Administrator of the United States Environmental Protection Agency, Washington, DC (US)

( * ) Notice: Subject to any disclaimer, the term of this patent is extended or adjusted under 35 U.S.C. 154(b) by 0 days.

(21) Appl. No.: 09/297,235

(22) PCT Filed: Apr. 24, 1998

(86) PCT No.: PCT/US98/08279

§ 371 Date: Apr. 26, 1999

§ 102(e) Date: Apr. 26, 1999

(87) PCT Pub. No.: WO98/49280

PCT Pub. Date: Nov. 5, 1998

Related U.S. Application Data

(60) Provisional application No. 60/044,106, filed on Apr. 25, 1997.

(51) Int. Cl.[7] .................................. B09B 3/00; C12N 1/20
(52) U.S. Cl. ..................................... 435/262.5; 435/253.3; 435/875
(58) Field of Search .............................. 435/262.5, 253.3, 435/875

(56) References Cited

U.S. PATENT DOCUMENTS

| | | | |
|---|---|---|---|
| 5,055,402 | * 10/1991 | Greene et al. | 435/174 |
| 5,443,729 | * 8/1995 | Sly et al. | 210/611 |
| 5,512,702 | * 4/1996 | Ryan et al. | 588/256 |

OTHER PUBLICATIONS

Vesper et al. Water, Air and Soil Pollution. 1996. 86:207–219.*

Aickin et al. Micribios Letters. 1978. 9 (34), 55–66.*

ATCC Bacteria and Bacteriophages. Catalogue. 19 th edition. 1996, p. 277.*

* cited by examiner

*Primary Examiner*—Sandra E. Saucier
*Assistant Examiner*—Vera Afremova
(74) *Attorney, Agent, or Firm*—Glenna Hendricks; Alan M. Ehrlich

(57) ABSTRACT

Bioavailability of lead and other heavy metals in the environment may be reduced by addition of microorganisms which sequester lead from the environment in the presence of phosphate. The microorganisms are highly mobile and are, therefore, capable of scavenging a material for lead, which they then sequester. The method basically consists of reducing bioavailability of lead in the environment by addition of *Pseudomonas aeruginosa* strain CHL004 (ATCC 55937) to said environment in the presence of phosphate which contains at least stoichiometric equivalent amounts of phosphate to lead.

8 Claims, No Drawings

METHOD FOR REDUCING BIOAVAILABILITY OF LEAD BY A LEAD-SEQUESTERING SOIL BACTERIUM

This application is a 371 of PCT/US98/08279 filed Apr. 24, 1998 which claims benefit of Prov. No. 60/044,106 filed Apr. 25, 1997.

FIELD OF THE INVENTION

This invention relates to means of rendering environmental lead innocuous by assimilation into microorganisms. Using the methods of the invention, the lead is sequestered in an insoluble form. In addition, the organism is able to sequester other heavy metals such as cadmium and arsenic.

BACKGROUND OF THE INVENTION

Lead in the environment presents a significant health risk, especially to children. Lead-based paint from older buildings has been one of the primary sources of lead-caused morbidity. The ability of microorganisms to bioaccumulate or to remove heavy metals from aqueous systems has been noted. Applications have included removal of metals from sewage or industrial effluent and mining of precious heavy metals, and for recovering polluting metals from geothermal ponds. However, lead removal from soil can be more difficult due to the chemistry of binding mechanisms in the soil.

Vesper, et al, ("Microbial Removal of Lead from Solid Media and Soil". *Water, Air, & Soil Pollution*. 86:207–219 (1996) reported use of a strain of *Pseudomonas aeruginosa* (the organism used in the instant application) to remove lead from solidified media and soil. However, they did not report use of the organism in the presence of phosphate to provide an insoluble form of lead, but only reported that the organism could sequester lead. There is no suggestion therein that the organisms could sequester other heavy metals.

Ryan, et al, in U.S. Pat. No. 5,512,702, teaches that addition of calcium phosphate to lead-containing soil resulted in formation of insoluble lead phosphate. However, no use of any microorganisms is reported or suggested therein. Furthermore, the calcium phosphate required therein, while appropriate for use in soil, would not necessarily be appropriate for use in other ecosystems or in solutions containing lead or other heavy metals. Significant theoretical and experimental evidence supports the hypothesis that lead phosphates are the most insoluble and stable forms of Pb in soils. Among all the Pb-P minerals, chloropyromorphite has one of the lowest solubilities; thus it is one of the most stable under favorable environmental conditions (Nriagu, J. O., "Lead Orthophosphates-II. Stability of Chloropyromorphite at 25° C." *Geochim. Cosmochim. Acta*. 37:367–377 (1973)). Formation of chloropyro-morphite [$Pb_{10}(PO_4)_6Cl_2$] in soils contaminated through mining activities was reported by Cotter-Howells and Thornton ("Sources and Pathways of Environmental Lead to Children in a Derbyshire Mining Village." *Environ, Geochem, Health*. 12:127–135 (1991)). Further, they illustrated that the blood Pb levels of children exposed to these contaminated soils was not elevated thus implying that this form of soil Pb is unavailable.

SUMMARY OF THE INVENTION

The instant invention provides means of reducing bioavailability of lead in the environment by addition of microorganisms which sequester lead from the environment in the presence of phosphate. The microorganisms are highly mobile and are, therefore, capable of scavenging a material for lead, which they then sequester. The method basically consists of reducing bioavailability of lead in the environment by addition of *Pseudomonas aeruginosa* strain CHL004 to said environment in the presence of phosphate which contains at least stoichiometric equivalent amounts of phosphate to lead.

It has now been found that the organism described herein is capable of sequestering other heavy metals. Examples of such heavy metals include cadmium and arsenic. These metals may also be sequestered in the bacteria in the form of salts (not necessarily phosphate salts).

The organism may be grown on a solid matrix such as charcoal or a synthetic polymer. The matrix with the organism is then added to the substrate from which the heavy metal is to be extracted.

DETAILED DESCRIPTION OF THE INVENTION

The present invention provides improved means for converting bioavailable lead to phosphates which are no longer bioavailable. By conversion of the lead to insoluble lead compounds, the danger of lead poisoning is greatly reduced. The microorganism was isolated from soil samples obtained from the mouth of an abandoned lead mine in Northern Kentucky in Owen County near the city of Gratz on Lead Mine Road off SR 355. It has been deposited in the American Type Culture Collection (ATCC No. 55937).

While the method of Ryan, et al. (cited above) results in production of insoluble lead phosphate compounds, that method relies on the ability of lead to physically encounter sufficient phosphate so that the lead phosphates are formed. Because the *Pseudomonas aeruginosa* strain CHL004 is a highly mobile organism, it is capable of scavenging lead. Since the organism "seeks out" the lead in the substrate, the process of the invention is not solely dependent on the mixing of the substrate, which may, for example, include soil or run-off from lead-contaminated environments, to effectively abate bioavailability of lead from the environments. Hence, the process is active and can occur over a greater area of soil.

Since biological processes are usually more "economical" in their use of raw materials, the utilization of phosphate would be more effective. The organism has not been genetically constructed, but is a product found in nature which has been isolated and cultured for its distictive metal-sequestering characteristics. The bacterial population can decrease when metals capable of being sequestered are relatively absent in the environment, but can then increase when contamination with lead reoccurs at the site. This adaptability is not seen in the Ryan method. The more efficient biological process, by making it possible to use less phosphate, would decrease likelihood of poisoning a system by excess phosphate.

In some environments where it is not possible to use the Ryan method because of physical or chemical attributes of the environment, bacteria can be utilized to sequester the lead and other heavy metals. For example, a high energy river (a physical characteristic) would not allow the environment for mixing and contacting of lead with the phosphate required in the process of Ryan. Looking to another example, a stream with a delicate ecosystem often will not support the chemical exposure to phosphates required by Ryan. Using the bacterial approach, it is possible to expose the lead-containing substrate to the active, scavenging organisms for sequestering without addition of phosphate in the form of calcium phosphate. It has also been found that the bacteria can be used to scavenge what residual lead has not been removed from a substrate after the practice of the Ryan procedure. This illustrates the value of the organism's ability to scavenge.

Several modes of application to the lead-containing substrate are possible. The organisms can be grown in large quantities, then added to the contaminated soil. The surface soil is then mixed with the bacteria, with phosphate added if phosphate is lacking in the soil. (Most lead contamination in the U.s. occurs in surface soils.)

The organism may also be embedded in a porous matrix such as small particles of foam or charcoal. This matrix could then be mixed with the contaminated material. After allowing time for the bacteria to sequester the heavy metal, the matrix with the bacteria and the target heavy metal can be removed from the contaminated material. The matrix could, additionally, contain a magnetic element such as iron. The matrix containing the iron and the bacteria sequestering the target metal could then be withdrawn from the contaminated material using magnetic means such as electromagnets.

The method of the invention would comprise the steps of (1) growing Pseudomonas aeruginosa strain CHL004 on a solid matrix, (2) adding the matrix prepared in step 1 to the environmental material containing the heavy metal, (3) allowing sufficient time for the bacteria to sequester the heavy metal from the environmental material, then (4) separating the matrix with the bacteria sequestering the heavy metal from the environmental material.

For deeper contamination, large quantities of the CHL004 could be added to hydraulic fractures. Using electrokinetic means, water containing lead could be driven into layers containing bacteria.

In another embodiment of the invention, heavy metalcontaining containing leachate could be processed through a matrix in the form of a filter containing the organism. The filter may be made of granular activated carbon or some other porous support upon which the organism is grown or in which they are imbedded. this would make it possible to allow the organisms to sequester the metal. It would then be possible to remove the matrix with the organisms having the metal sequestered therein. The matrix could then be exposed to an environment (probably a liquid) containing phosphate (in the case of lead) or other ions which would render the target metals insoluble.

The organism may also be placed in a mixer or reactor with contaminated soil or mine tailings. If the soil or tailings lack sufficient phosphate, a source of phosphate may be added.

The organism could also be added to municipal and hazardous solid waste to immobilize lead.

MATERIALS AND METHODS

Isolate CHL004 was grown on various media with 1 gm of lead nitrate per L of media at 30° C. for 1, 4 or 5 days. The bacteria concentrated lead most effectively at 5 days on Peptone Iron Agar (PIA) with lead nitrate. Concentrations of 0.05%, 0.075%, 0.175%, & 0.3 0% of ferric ammonium citrate (FAC) was added to the media to evaluate its effect on the lead particle concentrated in the bacterium using the JEOL JEM 1200EXII Electron Microscope with a Link exL energy dispersive x-ray spectrometry (EDXS) system and a 1% phosphotungstic acid stain. The Peptone Iron Agar was made by Defco laboratories of Detroit, Michigan. (This agar contains about $1.2 \times 10^{-1}$ gm/L phosphate.)

Electron microscopy showed that the concentration of ferric ammonium citrate in the medium correlates with both an increase of lead phosphate particles in each organism and in the percentage of organisms which concentrate the lead, when 0.05%, 0.075%, 0.175%, & 0.30% of ferric ammonium citrate were evaluated. It is possible that the mechanism of lead concentration is through the use of siderophores and is fortuitous.

Analysis could support the original hypothesis (Vesper et al., 1996) that the mechanism of concentration or formation of lead phosphate particles is twofold in nature. The curves of phosphorous and lead are not linear and indicate that there is initially a rapid and then a slower process as the amount of ferric ammonium citrate increases. Perhaps this organism utilizes two siderophores as Hu and Boyer's ("Siderophore-Mediated Aluminum Uptake by *Bacillus megaterium* ATTCC 19213. "*Applied and Environmental Microbiology.* 62:4044–4048 (1996)) aluminum concentrating bacteria does.

Cultures of *Pseudomonas aeruginosa* strain CHL004 are grown in yeast broth. In instances where solid matrix is desirable, the matrix may be suspended in the broth. The organism is then added to the broth and allowed to grow. The matrix with the organisms is then removed from the broth and placed into the environment containing the target heavy metal. The matrix may then be withdrawn from the environment and exposed to phosphate or other ions to allow conversion of the metal to a salt.

Means of Preparing on a Solid Support

Granulated activated carbon (GAC) is placed in a bioreactor. Nutrient broth with organisms to achieve $10^4$–$10^7$ CFU/ml CHL004 is added to the GAC in the bioreactor and allowed to grow thereon. The resulting GAC with nutrient and CHL004 is then mixed with soil containing lead.

To provide the organism on a polymeric support, the organism is grown in a reactor until concentration of the organism reaches $10^4$–$10^7$ CFU/ml CHL004. Monomeric urethane is added to the reactor followed by addition of finely divided iron and polymerizing agent to provide a sponge containing the organism and iron. The resulting material is added to water containing arsenic. After allowing reaction to occur (usually at least 24 hours) the water is swept with a magnet to remove the polymeric material containing the organisms, iron and arsenic.

Electron micrographs showed both large (more common) and small intracellular particles. The EDX spectrum of the particles confirms that they are lead phosphate minerals, similar in chemical composition to lead pyromorphite as Ma, et al. ("Insitu Lead Immobilization by Apatite." *Environ. Sci. Technol.* 27:1803–1810 (1993)) have seen.

The method of the invention is particularly useful when more than one heavy metal contaminates the environment. Such an example would be soil contaminated with both arsenic and lead.

The organisms useful in the practice of the inventive method are highly adaptable. However, a pH range of 5.5 to 8.5 is believed advantageous for their growth. The soil can be tested by standard agricultural methods used in soil analysis to determine pH and phosphate level. The amount of phosphate can then be increased if the soil is deficient. Additionally, the pH can be adjusted by usual means known in the agricultural arts by addition of acid or base to the substrate.

The use of the bacteria on porous materials such as charcoal may be particularly useful when it is not appropriate to add phosphate to the substrate. When the target metal is lead, the support with the bacteria containing the sequestered lead can be removed and placed in an environment that will provide sufficient phosphate for conversion of the lead to the insoluble phosphate before disposal.

What we claim is:

1. A method of reducing bioavailability of lead in a lead-contaminated environment comprising adding *Pseudomonas aeruginosa* strain CHL004 having the lead-sequestering properties of the organism identified as ATCC No. 55937 to said environment, either (1) after ascertaining that said environment contains sufficient phosphate to provide at least one stoichiometric equivalent amounts of phosphate to lead or (2) with addition of sufficient phosphate in ionic form to said environment to provide at least one stoichiometric equivalent amount of phosphate to lead.

2. A method of reducing lead in a lead-contaminated environmental material comprising the steps of
    (1) growing *Pseudomonas aeruginosa* strain CHL004 having the lead-sequestering properties of the organism identified as ATCC No. 55937 on a solid matrix,
    (2) adding the matrix prepared in step 1 along with sufficient phosphate in ionic form to provide at least a stoichiometric equivalent amount of phosphate to lead to the environmental material containing the lead,
    (3) allowing sufficient time for the bacteria to sequester the lead from the environmental material, then
    (4) separating the matrix with the bacteria sequestering the lead from the environmental material.

3. A method of claim 1 wherein the *Pseudomonas aeruqinosa* strain CHL004 is grown on a solid matrix.

4. A method of claim 3 wherein the matrix is activated carbon.

5. A method of claim 3 wherein the matrix forms a filter.

6. A method of claim 1 wherein said environment is lead-containing soil.

7. A method of claim 2 wherein the environmental material contaminated with lead is a liquid.

8. A method of claim 2 wherein matrix contains iron and the matrix with bacteria sequestering the heavy metal is removed by magnetic means.

* * * * *